(12) United States Patent
Cournoyer et al.

(10) Patent No.: US 8,475,499 B2
(45) Date of Patent: Jul. 2, 2013

(54) ROD TO ROD CONNECTORS AND METHODS OF ADJUSTING THE LENGTH OF A SPINAL ROD CONSTRUCT

(75) Inventors: John R. Cournoyer, Norfolk, MA (US); John Christian Barrett, Flemington, NJ (US); Leigh W Potter, Plymouth, MA (US); Alfred Fichera, Raynham, MA (US)

(73) Assignee: DePuy Synthes Products, LLC., Raynham, MA (US)

( * ) Notice: Subject to any disclaimer, the term of this patent is extended or adjusted under 35 U.S.C. 154(b) by 921 days.

(21) Appl. No.: 11/776,909

(22) Filed: Jul. 12, 2007

(65) Prior Publication Data

US 2008/0027436 A1  Jan. 31, 2008

Related U.S. Application Data

(60) Provisional application No. 60/807,377, filed on Jul. 14, 2006.

(51) Int. Cl.
*A61B 17/70* (2006.01)

(52) U.S. Cl.
USPC ..................................................... 606/260

(58) Field of Classification Search
USPC .............. 606/246–279; 623/17.16; 403/43, 403/59, 83, 300, 169–171, 306
IPC ....................................................... A61B 17/70
See application file for complete search history.

(56) References Cited

U.S. PATENT DOCUMENTS

| 270,478 | A | | 1/1883 | Pumphrey | |
|---|---|---|---|---|---|
| 721,411 | A | | 2/1903 | Alexander | |
| 1,647,802 | A | | 11/1927 | Joseph | |
| 2,278,320 | A | * | 3/1942 | Kath | 403/44 |
| 2,333,033 | A | | 10/1943 | Mraz | |
| 2,360,019 | A | * | 10/1944 | Ryan et al. | 403/44 |
| 3,900,025 | A | | 8/1975 | Barnes, Jr. | |
| 4,034,746 | A | | 7/1977 | Williams | |
| 4,386,603 | A | | 6/1983 | Mayfield | |
| 4,611,582 | A | * | 9/1986 | Duff | 606/258 |
| 4,658,809 | A | * | 4/1987 | Ulrich et al. | 606/258 |
| 4,747,394 | A | | 5/1988 | Watanabe | |
| 4,780,018 | A | * | 10/1988 | Godden | 403/173 |
| 4,827,918 | A | | 5/1989 | Olerud | |
| 4,887,596 | A | * | 12/1989 | Sherman | 606/305 |

(Continued)

OTHER PUBLICATIONS

Engineering print for Isola Extended Tandem Connector, Acromed Corporation, 1998.*

(Continued)

*Primary Examiner* — Ellen C Hammond

(57) ABSTRACT

A connector for connecting a first spinal rod to a second spinal rod includes a body having a first end and a second end spaced apart from the first end. The first end of the body has a first rod opening formed therein for receiving the first spinal rod and the second end has a second rod opening formed therein for receiving the second rod. The body of the connector has a passage extending between the first opening and the second opening. The body of the connector has a plurality of spaced apart adjustment openings oriented along the length of the body between the first end and the second end, the adjustment openings communicating with the passage to facilitate adjustment of the first and second spinal rods within the passage.

14 Claims, 21 Drawing Sheets

U.S. PATENT DOCUMENTS

| | | | |
|---|---|---|---|
| 4,926,849 A | | 5/1990 | Downey |
| 4,929,247 A | | 5/1990 | Rayhack |
| 4,931,055 A | | 6/1990 | Bumpus |
| 5,088,245 A | * | 2/1992 | Anderson ............................ 52/82 |
| 5,116,334 A | * | 5/1992 | Cozad et al. .................... 606/250 |
| 5,129,903 A | | 7/1992 | Luhr |
| 5,133,716 A | | 7/1992 | Plaza |
| 5,154,718 A | * | 10/1992 | Cozad et al. .................... 606/252 |
| 5,167,662 A | | 12/1992 | Hayes |
| 5,290,288 A | | 3/1994 | Vignaud |
| 5,468,241 A | | 11/1995 | Metz Stavenhagen |
| 5,474,207 A | * | 12/1995 | Nouhra .......................... 220/653 |
| 5,540,696 A | | 7/1996 | Booth, Jr. |
| 5,571,192 A | * | 11/1996 | Schonhoffer .............. 623/17.11 |
| 5,643,260 A | * | 7/1997 | Doherty ......................... 606/270 |
| 5,658,284 A | * | 8/1997 | Sebastian et al. ............. 606/278 |
| 5,700,263 A | | 12/1997 | Schendel |
| 5,765,957 A | * | 6/1998 | Connell ........................... 403/46 |
| 5,885,283 A | | 3/1999 | Gittleman |
| 5,899,903 A | | 5/1999 | Cotrel |
| 5,914,137 A | * | 6/1999 | Schmid ....................... 425/129.1 |
| 6,113,600 A | | 9/2000 | Drummond |
| 6,126,660 A | | 10/2000 | Dietz |
| 6,332,887 B1 | | 12/2001 | Knox |
| 6,432,108 B1 | | 8/2002 | Burgess |
| 6,447,545 B1 | * | 9/2002 | Bagby ......................... 623/17.16 |
| 6,451,019 B1 | | 9/2002 | Zucherman |
| 6,645,206 B1 | * | 11/2003 | Zdeblick et al. ............ 623/17.16 |
| 6,648,891 B2 | | 11/2003 | Kim |
| 6,663,631 B2 | * | 12/2003 | Kuntz ............................... 606/60 |
| 6,761,721 B2 | | 7/2004 | Burgess |
| 6,899,734 B2 | * | 5/2005 | Castro et al. ................ 623/17.16 |
| 7,011,658 B2 | | 3/2006 | Young |
| 7,029,472 B1 | * | 4/2006 | Fortin ............................... 606/60 |
| 7,066,938 B2 | | 6/2006 | Slivka |
| 7,175,622 B2 | * | 2/2007 | Farris ............................ 606/250 |
| 7,214,226 B2 | | 5/2007 | Alleyne |
| 7,537,596 B2 | * | 5/2009 | Jensen ........................... 606/280 |
| 7,699,874 B2 | * | 4/2010 | Young ........................... 606/250 |
| 7,744,634 B2 | | 6/2010 | Farris |
| 7,927,357 B2 | | 4/2011 | Sacher |
| 7,942,908 B2 | | 5/2011 | Sacher |
| 2002/0055782 A1 | * | 5/2002 | Bagby ......................... 623/17.16 |
| 2003/0167059 A1 | | 9/2003 | Young |
| 2004/0069517 A1 | * | 4/2004 | Olson .............................. 174/49 |
| 2005/0277926 A1 | | 12/2005 | Farris |
| 2007/0191841 A1 | * | 8/2007 | Justis et al. ...................... 606/61 |

OTHER PUBLICATIONS

Isola Brochure—Pediatric Isola Spinal System, Acromed Corporation, 1998.

* cited by examiner

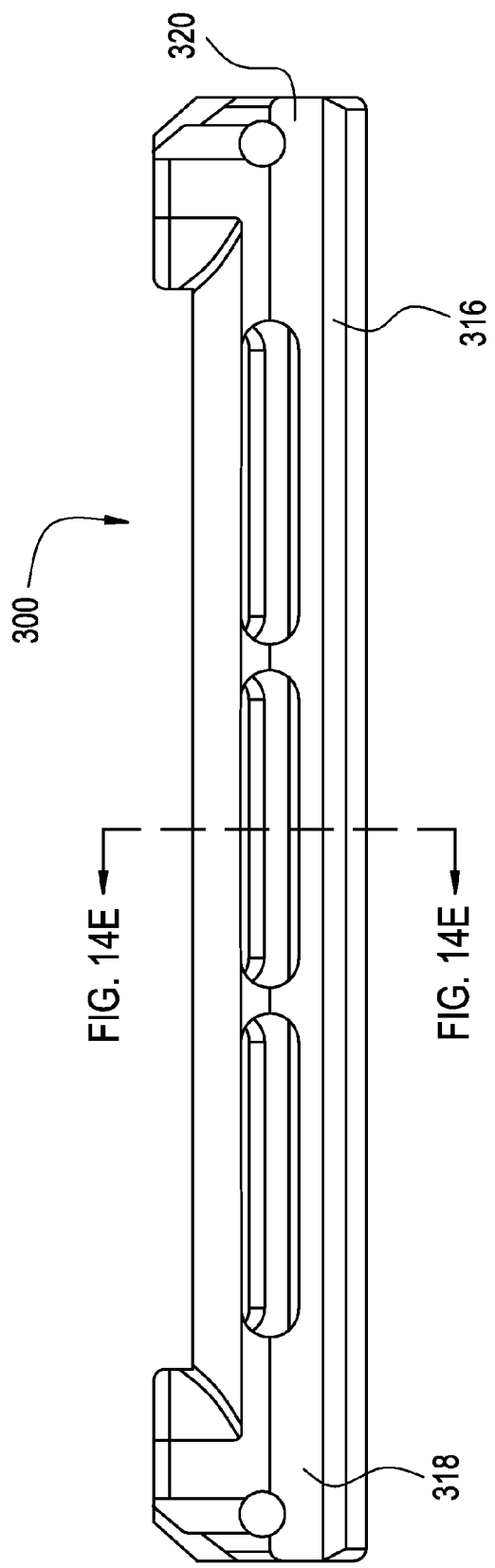

ROD TO ROD CONNECTORS AND METHODS OF ADJUSTING THE LENGTH OF A SPINAL ROD CONSTRUCT

REFERENCE TO RELATED APPLICATION

The present application claims priority to U.S. Provisional Patent Application No. 60/807,377, filed Jul. 14, 2006, which is incorporated herein by reference.

BACKGROUND

Spinal rods typically used in fusion surgery are generally contoured, placed into bone anchors, e.g., bone screws, hooks, etc., anchored to the vertebra of the spine, and secured to the bone anchors with one or more fasteners. Once implanted, the length of the spinal rod is fixed and is not adjustable during or after the initial surgery to gain additional correction or, in the case of pediatric patients, to allow for growth of the patient.

To alleviate this problem, a single spinal rod in a unilateral and/or a bi-lateral construct may be replaced with two or more spinal rods connected by a rod-to-rod connector that allows the rods to be adjusted relative to the connector and each other. The rods may be compressed or distracted relative to one another to achieve the desired correction and length. Such a rod-to-rod connector is available in DePuy Spine's Pediatriac Isola Spinal System.

There is a need for improved rod-to-rod connectors that facilitate connection of two spinal rods and the subsequent adjustment of the rods relative to one another.

SUMMARY

Disclosed herein are rod-to-rod connectors for connecting two rods of a spinal construct and for facilitating adjustment of the rods in vivo and methods of connecting and adjusting two rods relative to each other through a rod-to-rod connector.

In accordance with one exemplary embodiment, a connector for connecting a first spinal rod to a second spinal rod may comprise a body having a first end and a second end spaced apart from the first end. The first end of the body may have a first rod opening formed therein for receiving the first spinal rod and the second end of the body may have a second rod opening formed therein for receiving the second rod. The body of the connector may have a passage extending between the first opening and the second opening. The body of the connector may have a plurality of spaced apart adjustment openings oriented along the length of the body between the first end and the second end, the adjustment openings communicating with the passage. The body of the connector may have a first closure mechanism receiving opening positioned proximate the first end and communicating with the passage and a second closure mechanism receiving opening positioned proximate the second end and communicating with the passage.

In accordance with one exemplary embodiment, a method of adjusting two spinal rods of a spinal construct may comprise making an incision in a patient and accessing a rod to rod connector of a spinal construct, releasing at least one of a first rod and a second rod connected by the connector to permit adjustment of at least one of a first rod and second rod in a passage of the connector, inserting a distal end of an adjustment instrument into a first adjustment opening in the connector and adjusting the position of at least one of the first spinal rod and the second spinal rod within the passage of the connector, inserting the distal end of the adjustment instrument into a second adjustment opening in the connector, spaced from the first adjustment opening, and adjusting the position of at least one of the first spinal rod and the second spinal rod within the passage of the connector, and securing the position of the adjusted spinal rod within the passage of the connector.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

FIG. 14A is a side view of another exemplary embodiment of a connector for connecting two spinal rods;

DETAIL DESCRIPTION OF EXEMPLARY EMBODIMENTS

Figure 1:
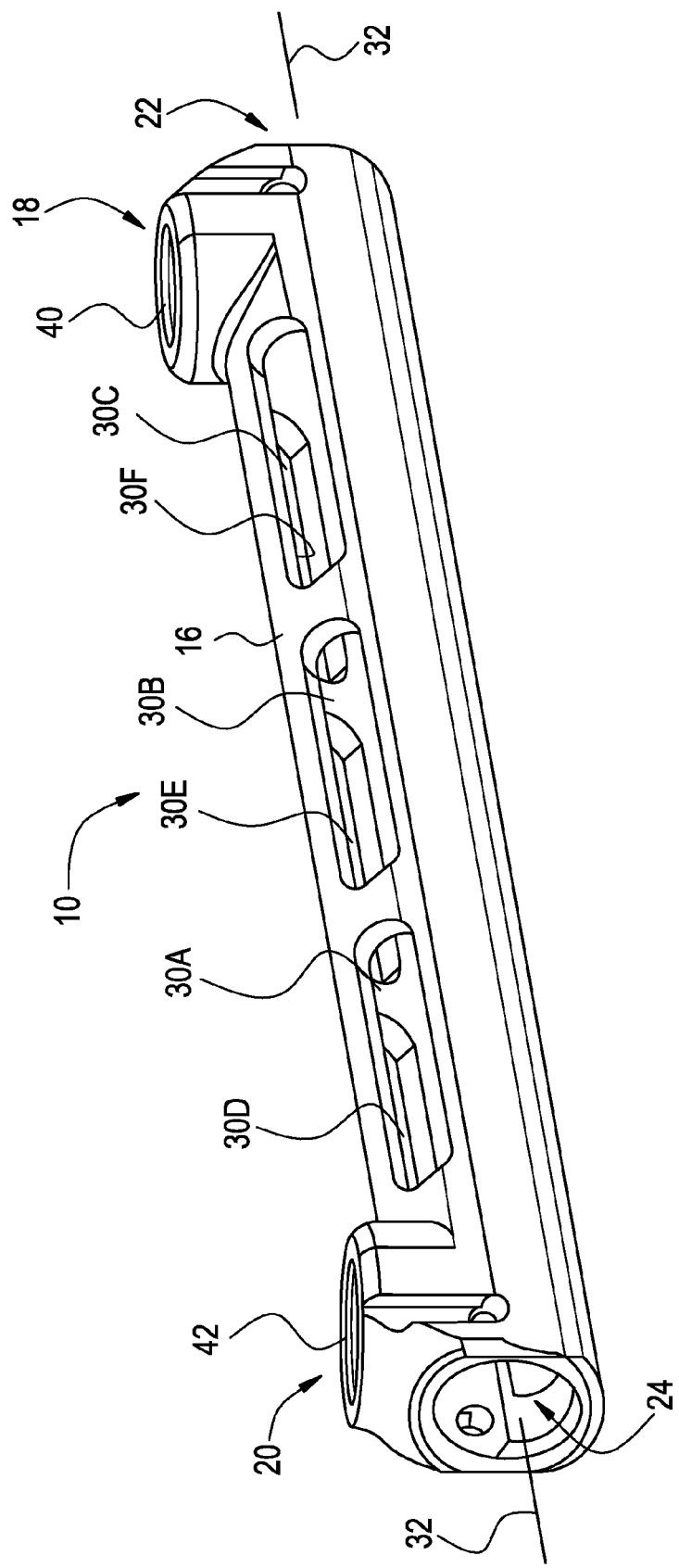
FIG. 1 is a perspective view of an exemplary embodiment of a connector for connecting two spinal rods.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a rod-to-rod connector 10 for connecting a first spinal rod 12 to a second spinal rod 14 in an end-to-end, e.g., tandem, arrangement for permitting subsequent adjustment of one or both of the spinal rods 10, 14 relative to each other and to the connector 10. The exemplary connector may comprise a body 16 having a first end 18 and a second end 20 spaced apart from the first end 18 of the connector 10. The first end 18 of the body 16 of the exemplary connector 10 may have a first rod opening 22 formed therein for receiving the first spinal rod 12 and the second end 20 of the body 16 may have a second rod opening 24 formed therein for receiving the second rod 14. The body 16 of the connector 10 may have a passage extending between the first rod opening 22 and the second rod opening 24 in which a portion of the first rod 12 and a portion of the second rod 14 may be positioned.

In the exemplary embodiment, the body 16 of the connector 10 is approximately cylindrical in shape and the passage, including the first and second rod openings 22, 24, is approximately cylindrical in shape, each having an approximately circular cross section. In alternative embodiments, the body 16 and/or the passage within the body 16 may have different shapes. For example, the body 16 and/or the passage within the body 16, including the first and second rod openings 22, 24, may have a polygonal, square, elliptical, rectilinear, or other suitable cross sectional shape. Preferably, the passage, including the first and second rod openings 22, 24, has a cross sectional shape approximately corresponding to the cross sectional shape of the spinal rod received thereby. In the exemplary embodiment, for example, the first rod opening 22, the second rod opening 24, and the passage therebetween have an approximately circular cross section approximately corresponding in size and shape to the first spinal rod 12 and second spinal rod 14, respectively. In certain exemplary embodiments, the first rod opening 22, the second rod opening 24, and the passage therebetween may be approximately corresponding in size and shape. In the exemplary embodiment illustrated in FIGS. 1-5, the first rod opening 22, the second rod opening 24, and the passage therebetween are equivalent in size and shape to receive and connect a first spinal rod 12 and a second spinal rod 14 that are equivalent in size and shape. In other exemplary embodiments, the first rod opening 22, the second rod opening 24, and portions of the passage therebetween may be distinct in size and shape to receive and connect two spinal rods of different size and/or shape, for example, to receive and connect a spinal rod having a square cross section with a cylindrical spinal rod having a circular cross section or to receive and connect a 4.5 mm diameter cylindrical spinal rod to a 5.5 mm diameter cylindrical spinal rod. In the illustrated exemplary embodiment, the passage within the body extends uninterrupted between the first rod opening 22 and the second rod opening 24. In other exemplary embodiments, the body 16 of the connector 10 may have a first passage opening at the first rod opening and a second passage opening at the second rod opening, wherein the first passage and the second passage are interrupted, i.e., are not connected.

The body 16 of the connector 10 may have a plurality of spaced apart adjustment openings 30 oriented along the length of the body 16 between the first end 18 and the second end 20 of the body 16 of the connector 10. The adjustment openings 30 may communicate with the passage within the body 16, for example, to allow a portion of an adjustment instrument or other instruments to access the passage and one or more rods positioned within the passage. The number of adjustment openings may vary depending on, for example, the length of the body 16 of the connector 10 and the size of the adjustment openings 30. For embodiments with a longer length body 16, preferably, two or more adjustment openings are provided and for embodiments with a shorter length body 16, one adjustment opening may be provided, as illustrated in FIG. 13. The space between adjacent adjustment openings 30 may be constant, as in the illustrated embodiment, or may be distinct. In certain exemplary embodiments, such as the exemplary embodiment illustrated in FIGS. 1-5, a set of adjustment openings 30 may be arranged linearly in an orientation parallel to the longitudinal axis 32 of the passage of the body 16. One or more sets of adjustment openings may be provided. In the illustrated embodiment, for example, two sets of adjustment openings may be provided—a first set of adjustment openings 30A-C and a second set of adjustment openings 30D-F. In other exemplary embodiments, a set of adjustment openings may be arranged non-linearly and/or such that a portion of two or more adjustment openings overlap at a segment of the passage.

Continuing to refer to FIGS. 1-5, the body 16 of the connector 10 may have a first closure mechanism receiving opening 40 and a second closure mechanism receiving opening 42. The first closure mechanism receiving opening 40 may communicate with the passage receiving the first spinal rod 12 to allow delivery of a closure mechanism for locking the position of the first spinal rod 12 within the passage. The second closure mechanism receiving opening 42 may communicate with the passage receiving the second spinal rod 14 to allow delivery of a closure mechanism for locking the position of the second spinal rod 14 within the passage. The size and shape of the first closure mechanism receiving opening 40 and the second closure mechanism receiving opening 42 may be selected to receive any know closure mechanism for locking a spinal rod to a spinal implant such as a bone anchor, a cross connector, or a bone plate. Such conventional closure mechanisms include, for example, a set screw that may be threaded directly, or indirectly through a compression member, into contact with the spinal rod to lock the rod in a desired position. In the illustrated exemplary embodiment, for example, the first closure mechanism receiving opening 40 and the second closure mechanism receiving opening 42 are configured to receive a set screw. In particular, the first closure mechanism receiving opening 40 and the second closure mechanism receiving opening 42 include internal threads for threaded engagement with a respective set screw. The first closure mechanism receiving opening 40 and the second closure mechanism receiving opening 42 may be configured to receive similar closure mechanisms, as in the illustrated exemplary embodiment, or distinct closure mechanisms. The first closure mechanism receiving opening 40 and the second closure mechanism receiving opening 42 may be positioned anywhere along the length of the body 16 of the connector 10. In the illustrated exemplary embodiment, the first closure mechanism receiving opening 40 is positioned proximate the first end 18 of the body 16 of the connector 10 and the second closure mechanism receiving opening 42 is positioned proximate the second end 20 of the body 16 of the connector 10.

Figure 11:
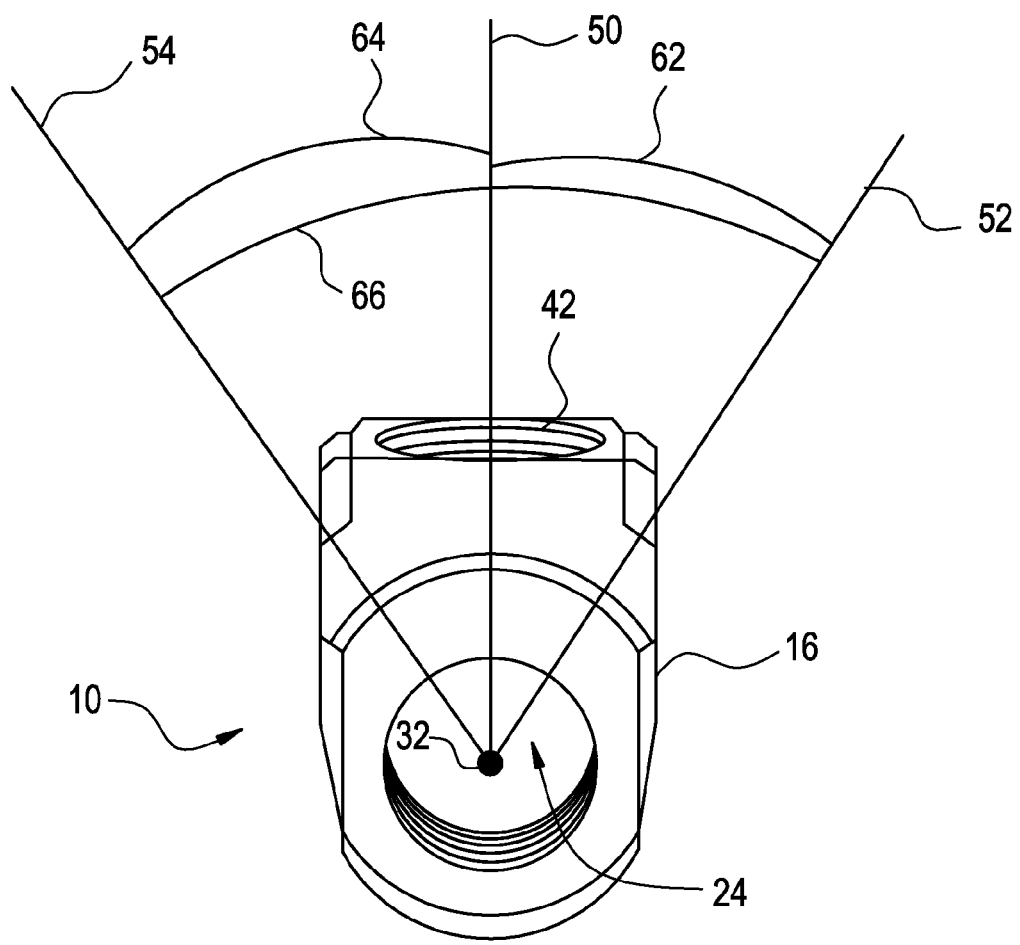
FIG. 11 is an end view of the connector of FIG. 1.

The first closure mechanism receiving opening 40 and the second closure mechanism receiving opening 42 may be oriented to facilitate placement of the closure mechanisms from the top of the connector. For example, the first closure mechanism receiving opening 40 and the second closure mechanism receiving opening 42 may be oriented in a first plane 50 that intersects the longitudinal axis 32 of the passage and the top surface of the body 16 of the connector 10, as illustrated in FIG. 11.

The adjustment openings 30 may be oriented to facilitate access to the passage and the spinal rods therein from the top of the connector. Preferably, the first closure mechanism receiving opening 40 and the second closure mechanism receiving opening 42 and the adjustment openings 30 are oriented to facilitate access to the respective openings from the top of the connector preferably without necessitating rotation or other adjustment of the connector 10. A plurality of adjustment openings 30, such as the first set of adjustment openings 30A-30C of the exemplary embodiment, may be oriented in a second plane 52 that may intersect the first plane 50 and the adjustment openings 30. The second plane 52 may be oriented at a first angle 62 to the first plane 50. The first angle 62 may be greater than approximately 0 degrees. In certain exemplary embodiments, the first angle may be greater than or equal to approximately 0 degrees and less than approximately 90 degrees and preferably may be between approximately 20 degrees and approximately 70 degrees.

In certain exemplary embodiments, a second set of adjustment openings 30, for example, the second set of adjustment openings 30D-F, may be oriented in a third plane 54 that intersects the first plane 50 and the adjustment openings 30. The third plane 54 may be oriented at a second angle 64 to the first plane 50. The second angle 64 may be greater than approximately 0 degrees. In certain exemplary embodiments, the second angle 64 may be greater that approximately 0 degrees and less than approximately 90 degrees and preferably may be between approximately 20 degrees and approximately 70 degrees. The first angle 62 may be approximately equal to the second angle 64 or may be distinct from the second angle 64. The third plane 54 may be oriented at a third angle 66 to the second plane 52. The third angle is preferably greater than approximately 45 degrees and in the illustrated embodiment is approximately 90 degrees.

Figure 2:
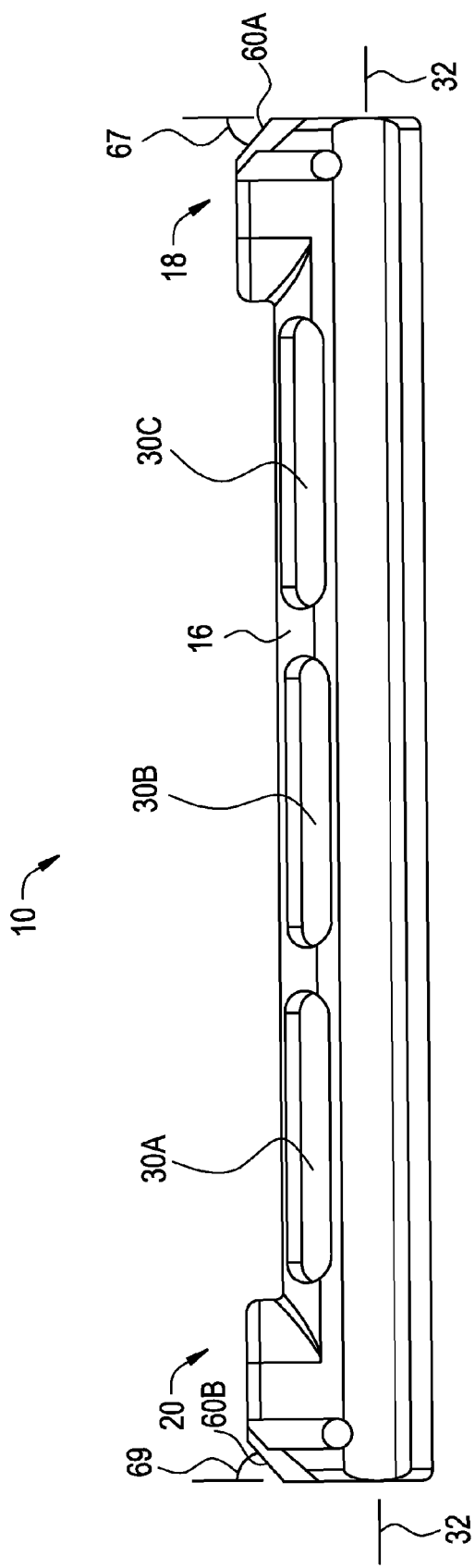
FIG. 2 is a side view of the connector of FIG. 1.
Figure 3:
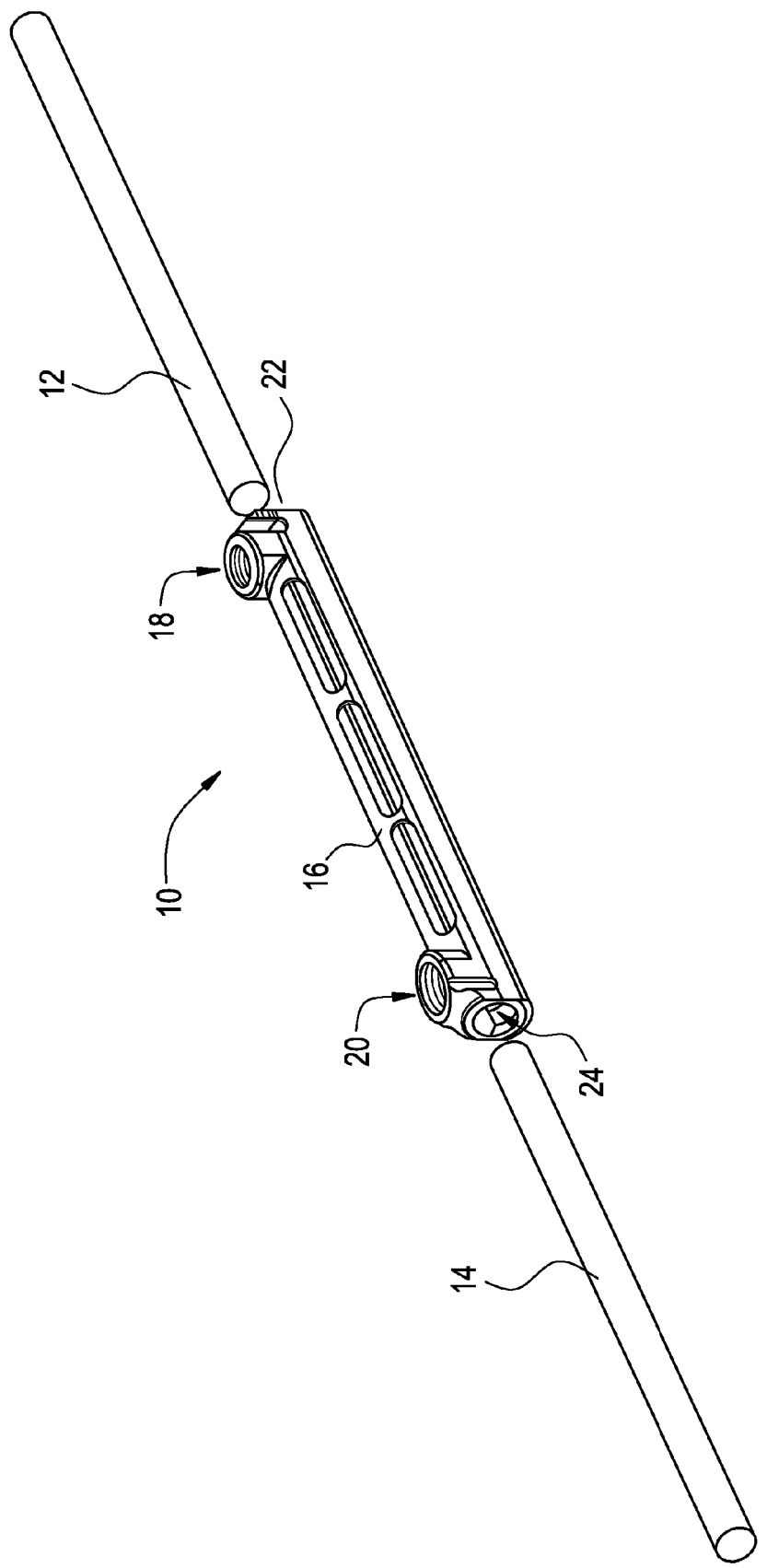
FIGS. 3 and 4 are perspective views of the connector of FIG. 1, illustrating the connector connecting two cylindrical spinal rods.
Figure 4:
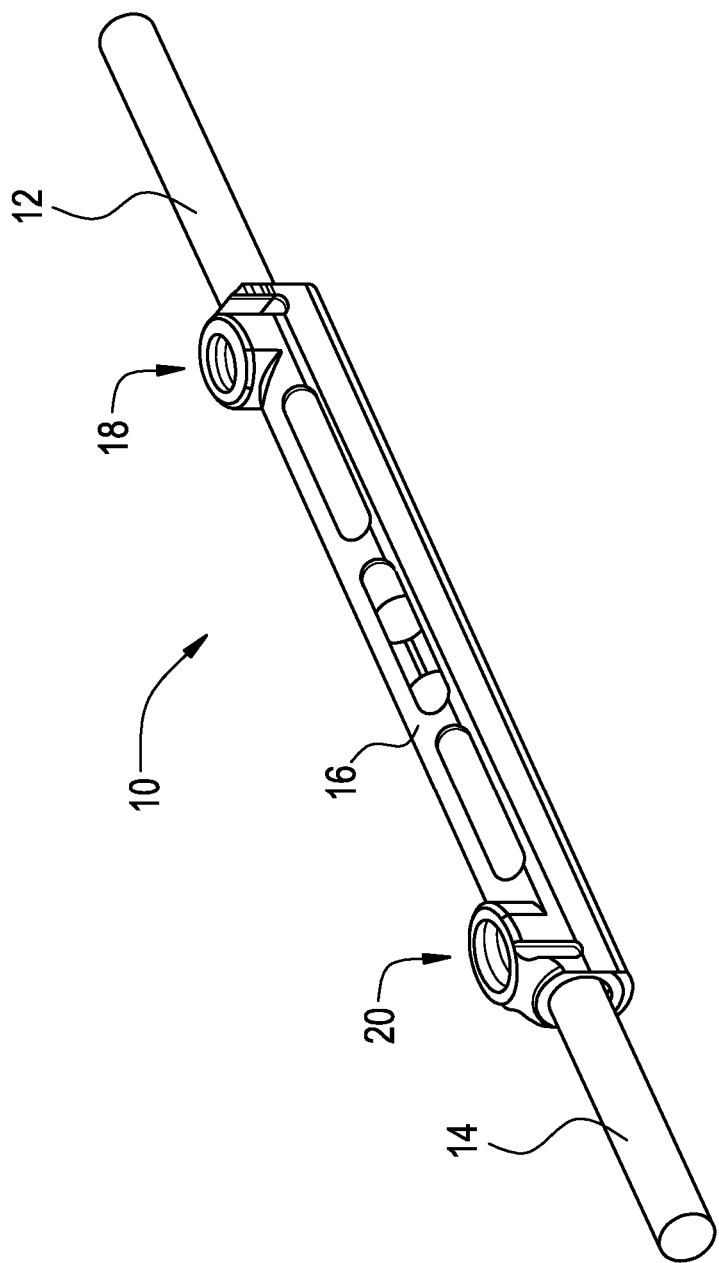
Figure 5:
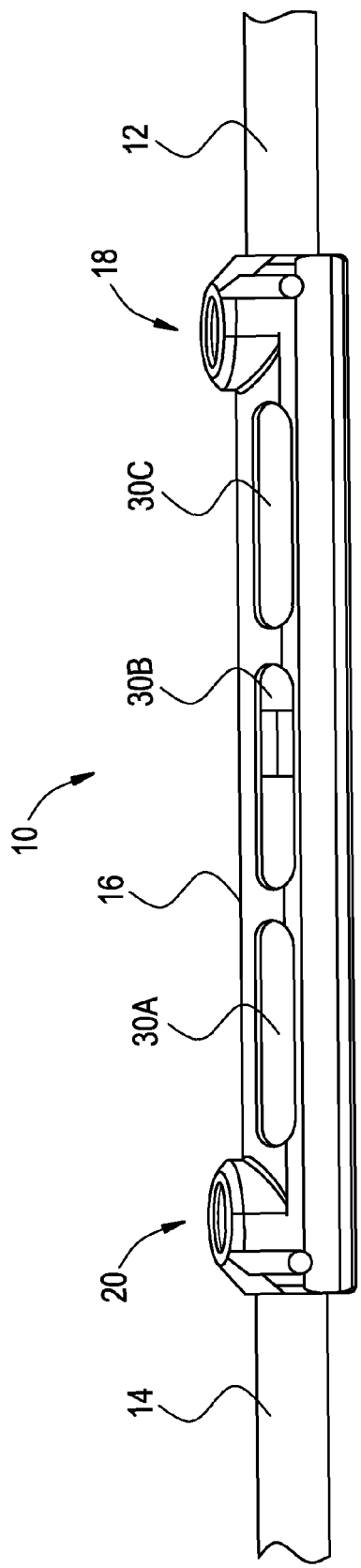
FIG. 5 is a side view of the connector of FIG. 1, illustrating the connector connecting two cylindrical spinal rods.

Referring to FIG. 2, the first end 18 and/or the second end 20 of the body 16 of the connector 10 can include a sloped surface 60 to facilitate positioning of the connector 10 relative to a spinal rod and to minimize trauma to body tissue during positioning of the connector 10. In the illustrated embodiment, the first end 18 includes a sloped surface 60a that is sloped at a first slope angle 67 to a line perpendicular to the longitudinal axis 32 of the passage. The second end 20 includes a sloped surface 60b that is sloped at a second slope angle 69 to a line perpendicular to the longitudinal axis 32 of the passage. The first slope angle 67 and the second slope angle 69 may be approximately equal, as in the illustrated embodiment, or may be distinct. The first slope angle 67 and the second slope angle 69 may be any angle sufficient to minimize tissue trauma. In certain embodiments, the first slope angle 67 and the second slope angle 69 may be greater than approximately 0 degrees and less than approximately 90 degrees and, preferably is greater than approximately 15 degrees.

The connector 10 may be constructed from any biocompatible material suitable for implantation in the body. Such materials may include metals and metal alloys, such as stainless steel and titanium, polymers, ceramics, or composites.

Figure 6:
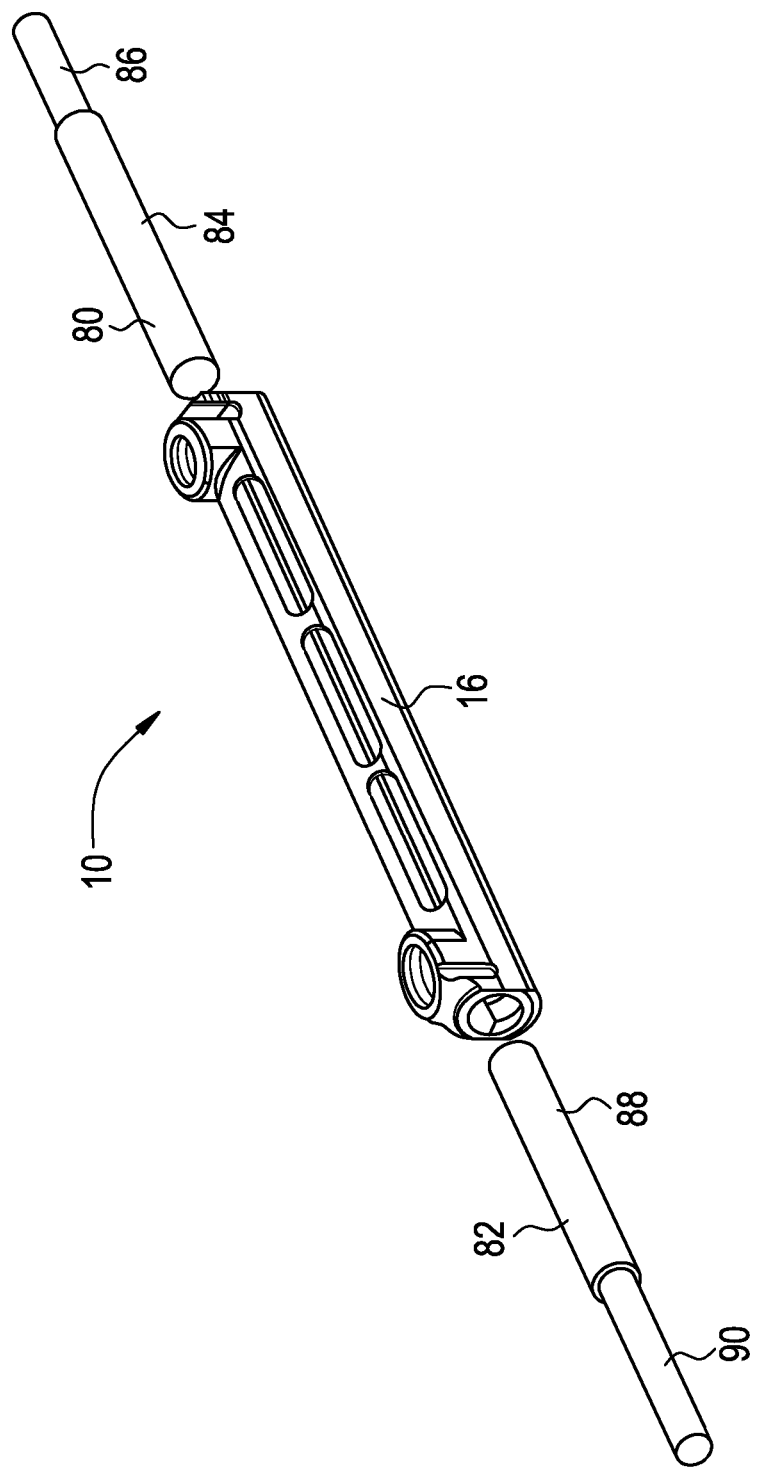
FIGS. 6 and 7 are perspective views of the connector of FIG. 1, illustrating the connector connecting two dual diameter spinal rods.
Figure 7:
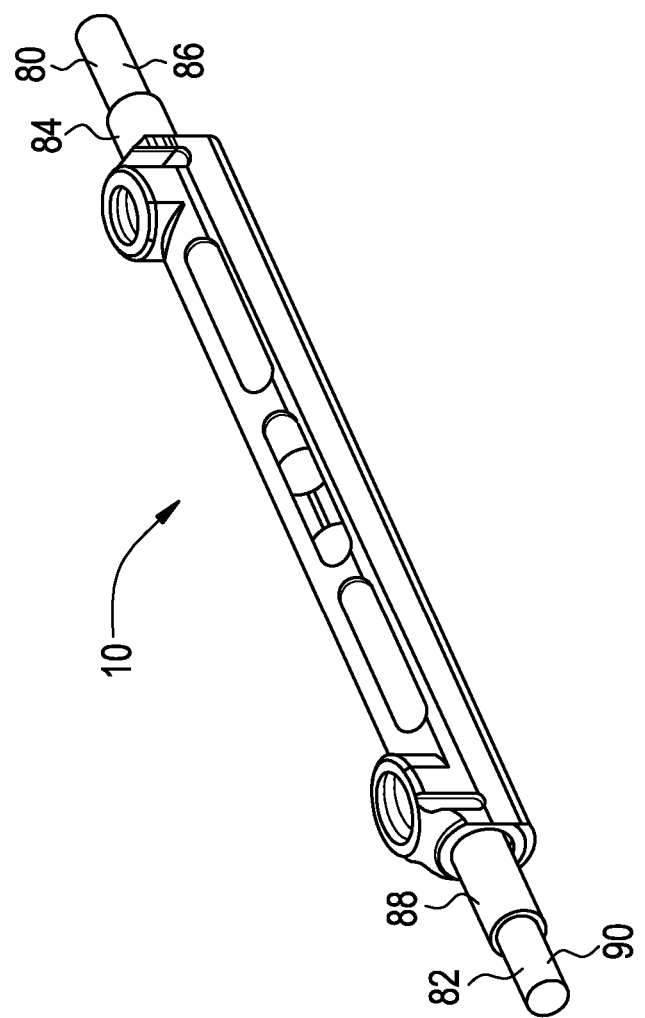
Figure 8:
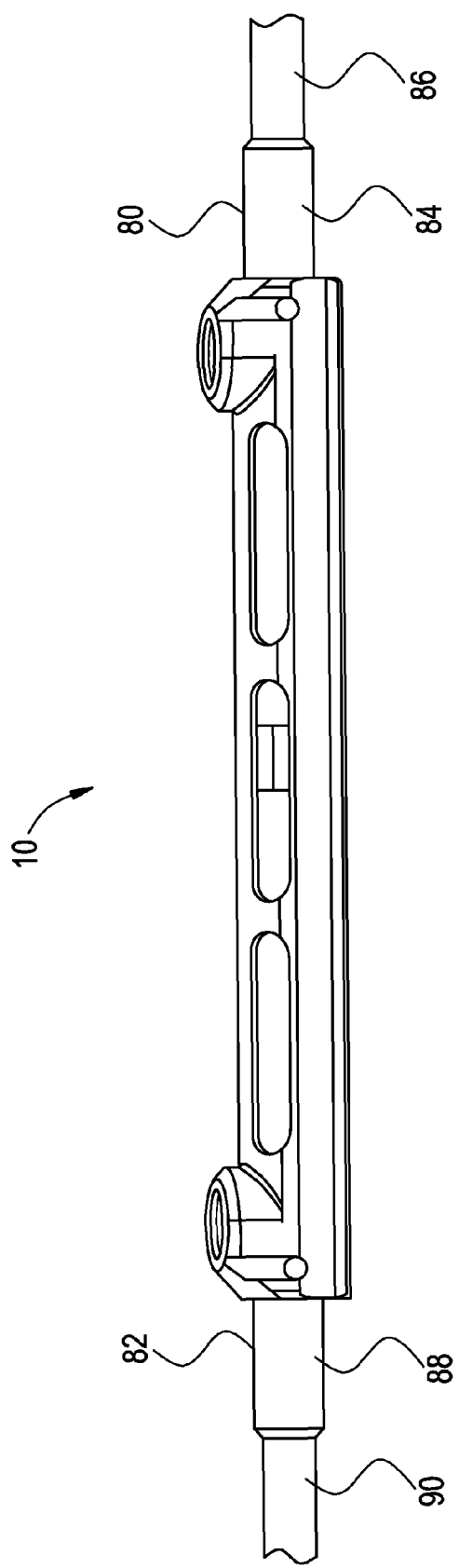
FIG. 8 is a side view of the connector of FIG. 1, illustrating the connector connecting two dual diameter spinal rods.

FIGS. 6-8 illustrate the connector 10 connecting a first dual diameter rod 80 to a second dual diameter rod 82. The first dual diameter rod 80 comprises a first segment 84 having a first diameter and a second segment 86 having a second diameter distinct from the first diameter. In the illustrated embodiment, for example, the first diameter is greater than the second diameter. In alternative embodiments, the second diameter may be greater than the first diameter. The second dual diameter rod 82 comprises a first segment 88 having a first diameter and a second segment 90 having a second diameter distinct from the first diameter. In the illustrated embodiment, for example, the first diameter is greater than the second diameter. In alternative embodiments, the second diameter may be greater than the first diameter.

The connectors disclosed herein may be used to connect two rods in an end-to-end, e.g., tandem, arrangement in a bilateral, unilateral or other construct. One exemplary method for connecting and adjusting two spinal rods may include positioning a first spinal rod 12 within the passage of the connector 10 through a first opening 22 at a first end 18 of the connector 10 and positioning a second spinal rod 12 within the passage of the connector 10 through a second opening 24 at a second end 20 of the connector 10. The rods may be positioned within the connector before or after the rods are implanted proximate the spine. If rods first are positioned proximate the spine and connected to bone anchors anchored to spinal anatomy, the first opening 22 may be positioned about an end of the first spinal rod 12 and the connector 10 may be advanced along the first spinal rod 12 and the second opening 24 may be positioned about the second spinal rod 14 and the connector 10 may be advanced along the second spinal rod 14 until the first spinal rod 12 and the second spinal rod 14 are in the desired position within the passage of the connector 10. In certain constructs, for example longer constructs, it may be desirable to utilize multiple connectors to connect three or more rods in an end-to-end arrangement.

An adjustment instrument may be used to adjust the position of the first spinal rod (e.g., 12, 80) and/or the second spinal rod (e.g., 14, 82) within the passage of the connector 10. For example, a distal end 100 of an adjustment instrument may be inserted into a first adjustment opening 30, for example, adjustment opening 30B, in the connector 10 to adjust the position of the first spinal rod 12 and/or the second spinal rod 14. If further adjustment is desired, the distal end 100 of the adjustment instrument may be inserted into a second adjustment opening in the connector, spaced from the first adjustment opening, for example, adjustment opening 30A and/or 30C, to adjust the position of the first spinal rod 12 and/or the second spinal rod 14. Subsequent adjustment(s) may be made through the same or additional adjustment openings. Once the spinal rods are adjusted to the desired position, the position of the first spinal rod 12 and/or the second spinal rod 14 within the passage of the connector 10 may be secured by operation of the closure mechanisms positioned within the first closure mechanism opening 40 and the second closure mechanism opening 42.

A distal end of the adjustment instrument may be inserted through one or more adjustment openings 30 to contact and adjust the first spinal rod 12 and/or the second spinal rod 14.

Figure 9:
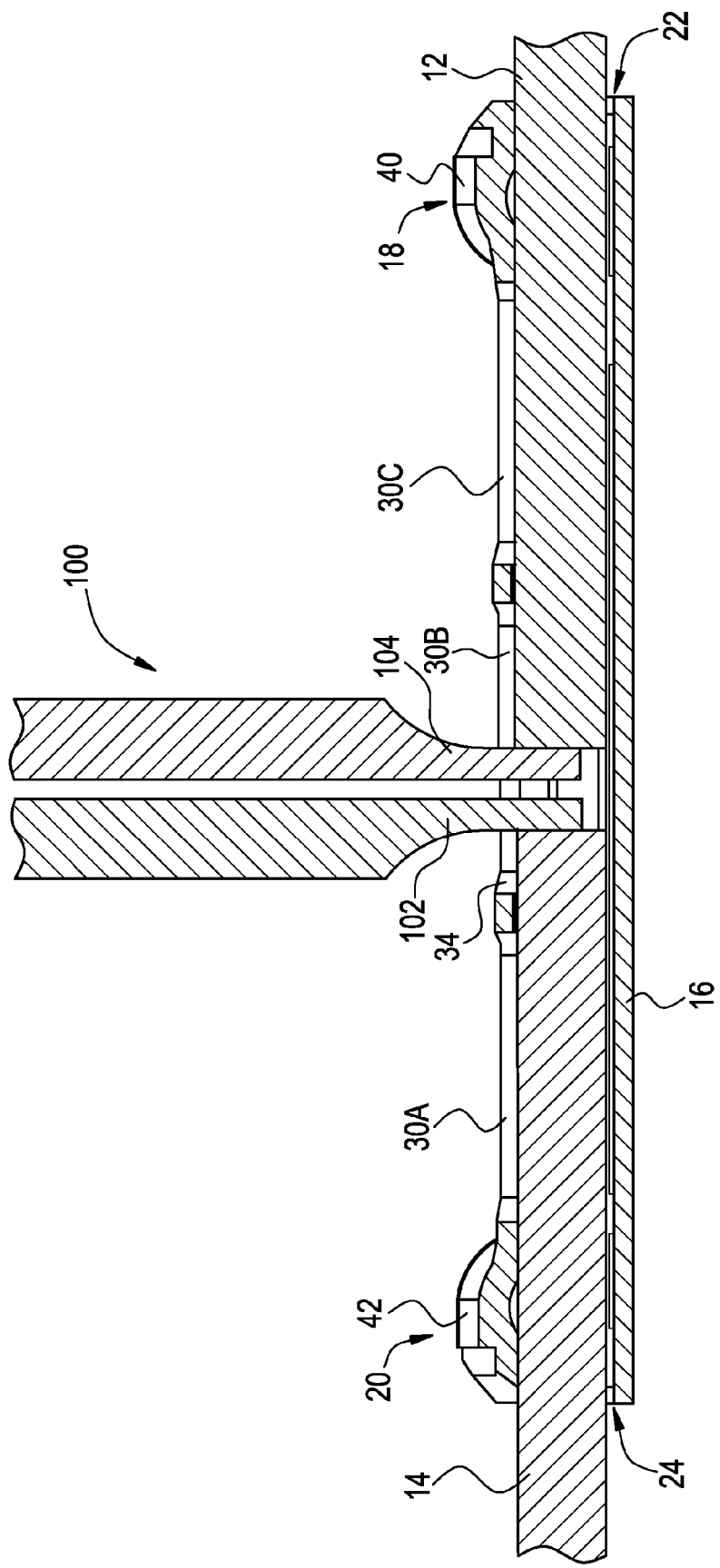
FIGS. 9 and 10 are side views in cross section of the connector of FIG. 1, illustrating the distal end of an exemplary adjustment instrument adjusting the two spinal rods within the passage of the connector.

Referring to FIG. 9, for example, a first component 102 of the distal end 100 of the adjustment instrument may be positioned through an adjustment opening 30 and against the second spinal rod 14. A second component 104 of the distal end 100 of the adjustment instrument may be positioned through the same or separate adjustment opening 30 as the first component 102 and against the first spinal rod 12. Separation of the first component 102 and the second component 104 may adjust the first spinal rod 12 and/or the second spinal rod 14 relative to one another.

Figure 10:
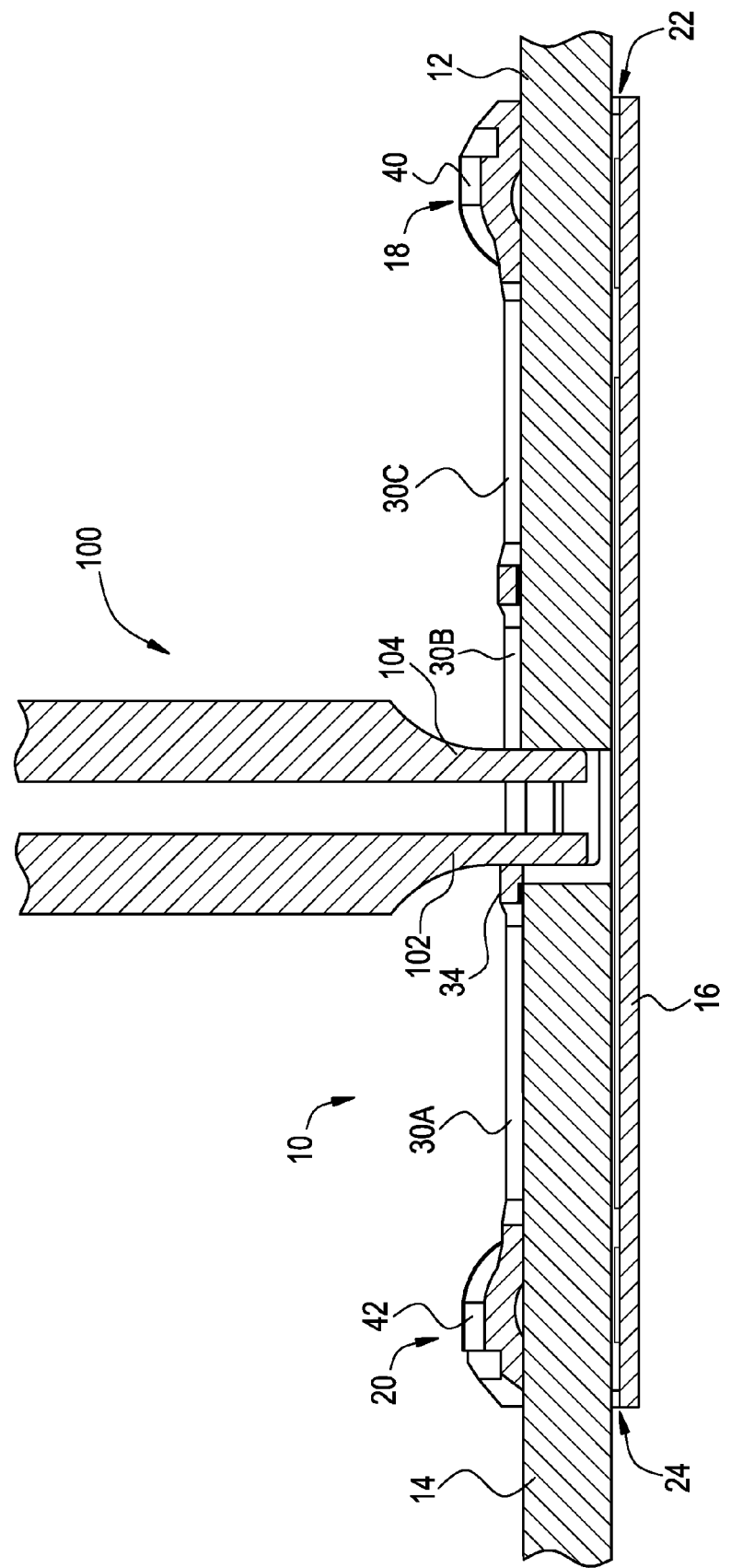

A distal end of the adjustment instrument may be inserted through one or more adjustment opening 30 to contact a portion of the connector 10 and a spinal rod to facilitate adjustment the first spinal rod 12 and the second spinal rod 14. Referring to FIG. 10, for example, a first component 102 of the distal end 100 of the adjustment instrument may be positioned through an adjustment opening 30 and against an edge 34 of an adjustment opening 30. A second component 104 of the distal end 100 of the adjustment instrument may be positioned through the same or separate adjustment opening 30 as the first component 102 and against the first spinal rod 12. Separation of the first component 102 and the second component 104 may adjust the first spinal rod 12 relative to the connector 10 and the second spinal rod 14.

Figure 12:
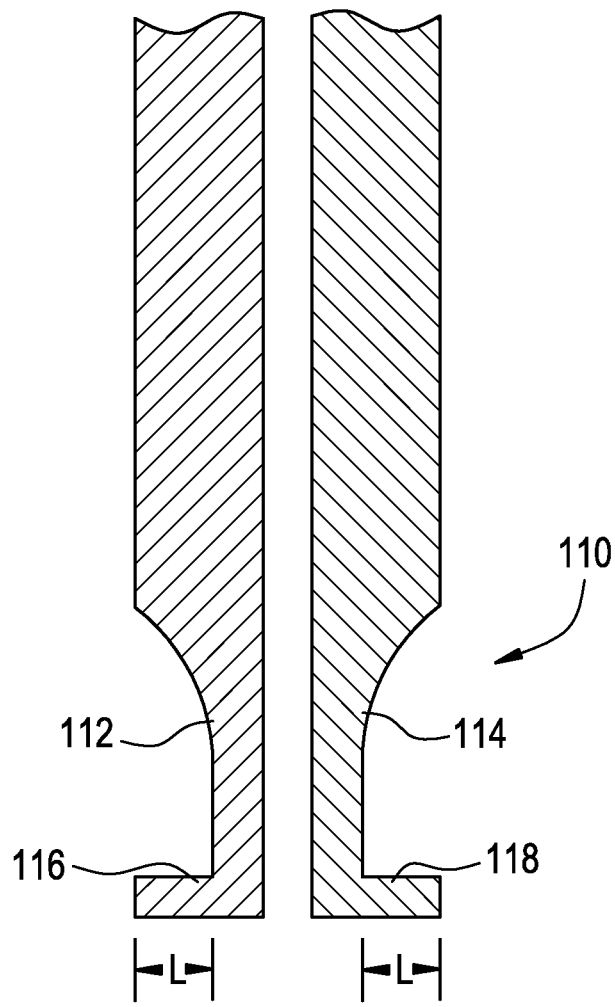
FIG. 12 is a side view of the distal end of an exemplary adjustment instrument.

To facilitate adjustment of a spinal rod through an adjustment opening 30, one or both of the components of the adjustment instrument may include a foot or like structure extending in a direction parallel to the longitudinal axis 32 of the passage of the connector when the distal end of the adjustment instrument in positioned through an adjustment opening. Referring to FIG. 12, for example, the distal end 110 of an adjustment instrument may include a first component 112 having a first foot 116 oriented approximately perpendicular to the first component 112 and a second component 114 having a second foot 118 oriented approximately perpendicular to the second component 114. The first foot 116 and the second foot 118 may be oriented parallel to each other and parallel to the longitudinal axis 32 of the passage of the connector 10 when the first foot 116 and the second foot 118 are positioned within the passage. The length L of the first foot 116 and the second foot 118 may be selected to be greater than or equal to the space between adjacent adjustment openings 30 of the connector 10. The first foot 116 and the second foot 118 may have the same or different lengths.

After a period of time from initial implantation, it may be desirable to adjust the position of the spinal rods connected by the connector, for example, to facilitate additional spinal correction or to compensate for growth of the patient. The connector 10 may be accessed by making an incision in the patient and creating a path through the patient's tissue to proximate the connector 10. Preferably, the connector 10 is accessed through minimally invasive surgical techniques to minimize trauma to surrounding tissue. For example, a small, puncture incision may be made and dilated by one or more dilators to create a pathway to the connector 10. A port, retractor, or other access device may be utilized to create and maintain the pathway to the connector 10. Once the connector 10 is accessed, the first spinal rod 12 and/or the second spinal rod 14 may be released to permit adjustment of one or both of the spinal rods within the passage of the connector. The spinal rods may be released by operation of a respective closure mechanism. The released spinal rod or rods then may be adjusted in any manner described above or by other methods, such as by adjusting the position of one or both rods by engaging a portion the rod external to the connector passage with an instrument, such as a rod clamp or a rod holder, and moving the instrument to thereby adjust the position of the rod relative to the connector. Upon completion of the adjustment, the adjusted spinal rod(s) may be secured to the connector 10 by operation of a respective closure mechanism.

Figure 13A:
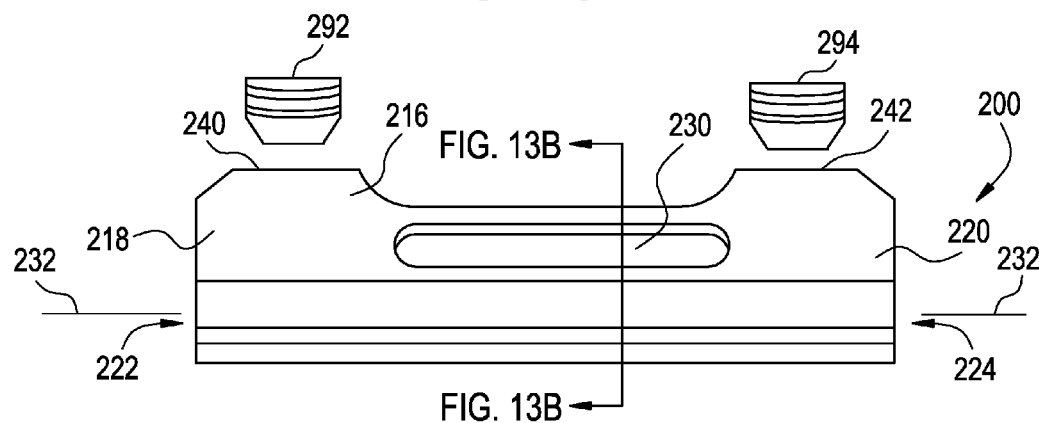
FIG. 13A is a side view of an exemplary embodiment of a connector for connecting two spinal rods having a single adjustment opening.
Figure 13B:
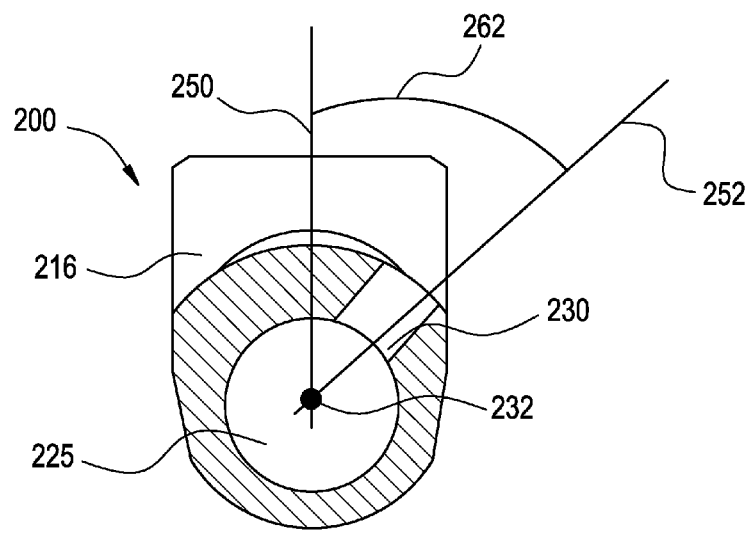
FIG. 13B is an end view in cross section of the connector of FIG. 13A taken along the lines B-B of FIG. 13A.

FIGS. 13A-B illustrate another exemplary embodiment of a rod-to-rod connector 200 for connecting a first spinal rod to a second rod in an end-to-end, e.g., tandem, arrangement for permitting subsequent adjustment of one or both of the spinal rods relative to each other and to the connector. The illustrated exemplary connector 200 may be similar in construction and use to the exemplary connector 10 discussed in detail above. For example, the exemplary connector 200 may comprise a body 216 having a first end 218 and a second end 220 spaced apart from the first end 218 of the connector 210. The first end 218 of the body 216 of the exemplary connector 200 may have a first rod opening 222 formed therein for receiving the first spinal rod and the second end 220 of the body 216 may have a second rod opening 224 formed therein for receiving the second rod. The body 216 of the connector 200 may have a passage 225 extending between the first rod opening 222 and the second rod opening 224 in which a portion of the first rod and a portion of the second rod may be positioned. The body 216 of the connector 200 may have a first closure mechanism receiving opening 240 and a second closure mechanism receiving opening 242. The first closure mechanism receiving opening 240 may communicate with the passage 225 receiving the first spinal rod to allow delivery of a closure mechanism, for example set screw 292, for locking the position of the first spinal rod within the passage 225. The second closure mechanism receiving opening 242 may communicate with the passage 225 receiving the second spinal rod to allow delivery of a closure mechanism, for example set screw 294, for locking the position of the second spinal rod within the passage 225. The first closure mechanism receiving opening 240 and the second closure mechanism receiving opening 242 may be oriented to facilitate placement of the closure mechanisms from the top of the connector. For example, the first closure mechanism receiving opening 240 and the second closure mechanism receiving opening 242 may be oriented in a first plane 250 that intersects the longitudinal axis 232 of the passage and the top surface of the body 216 of the connector 200, as illustrated in FIG. 13B.

In contrast to the connector 10, the exemplary connector 200 includes a single adjustment opening 230 oriented along the length of the body 216 of the connector 200 between the first end 218 and the second end 220 of the body 216 of the connector 200. The single adjustment opening 230 may communicate with the passage 225 within the body 216 in which a portion of the first rod and the second rod may be positioned to allow a portion of an adjustment instrument or other instruments to access the passage 225 and one or more rods within the passage 225. The adjustment opening 230 may be oriented to facilitate access to the passage 225 and the spinal rods therein from the top of the connector. Preferably, the first closure mechanism receiving opening 240 and the second closure mechanism receiving opening 242 and the adjustment opening 230 are oriented to facilitate access to the respective openings from the top of the connector preferably without necessitating rotation or other adjustment of the connector 200. The opening 230 may be oriented in a second plane 252 that intersects the first plane 250 and the adjustment opening 230. In the illustrated exemplary embodiment, the second plane 252 may intersect the first plane 250 proximate the longitudinal axis 232 of the passage 225. The second plane 252 may be oriented at a first angle 262 to the first plane 250. The first angle 262 may be greater than approximately 0 degrees. In certain exemplary embodiments, the first angle 262 may be greater than approximately 0 degrees and less than or equal to approximately 90 degrees and preferably may be between approximately 20 degrees and approximately 70 degrees.

Figure 14B:
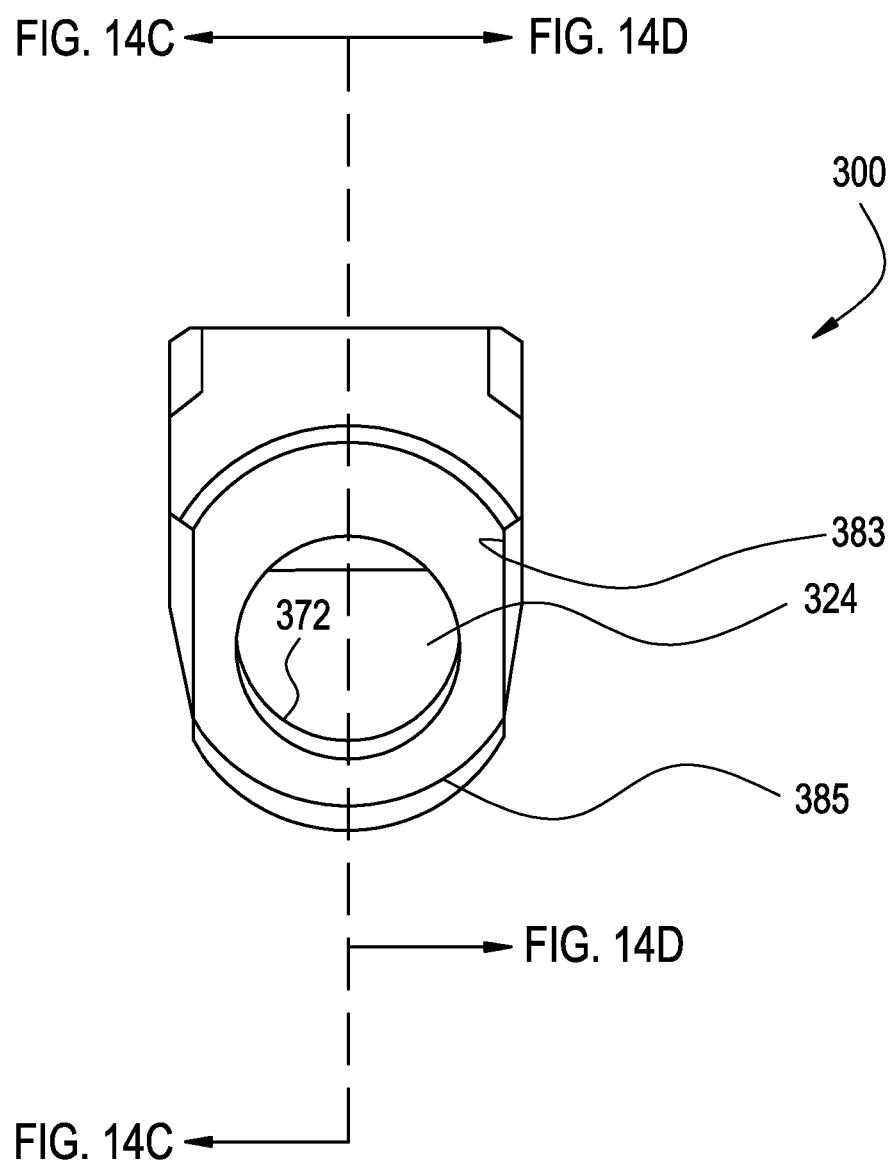
FIG. 14B is an end view of the connector of FIG. 14A.
Figure 14C:
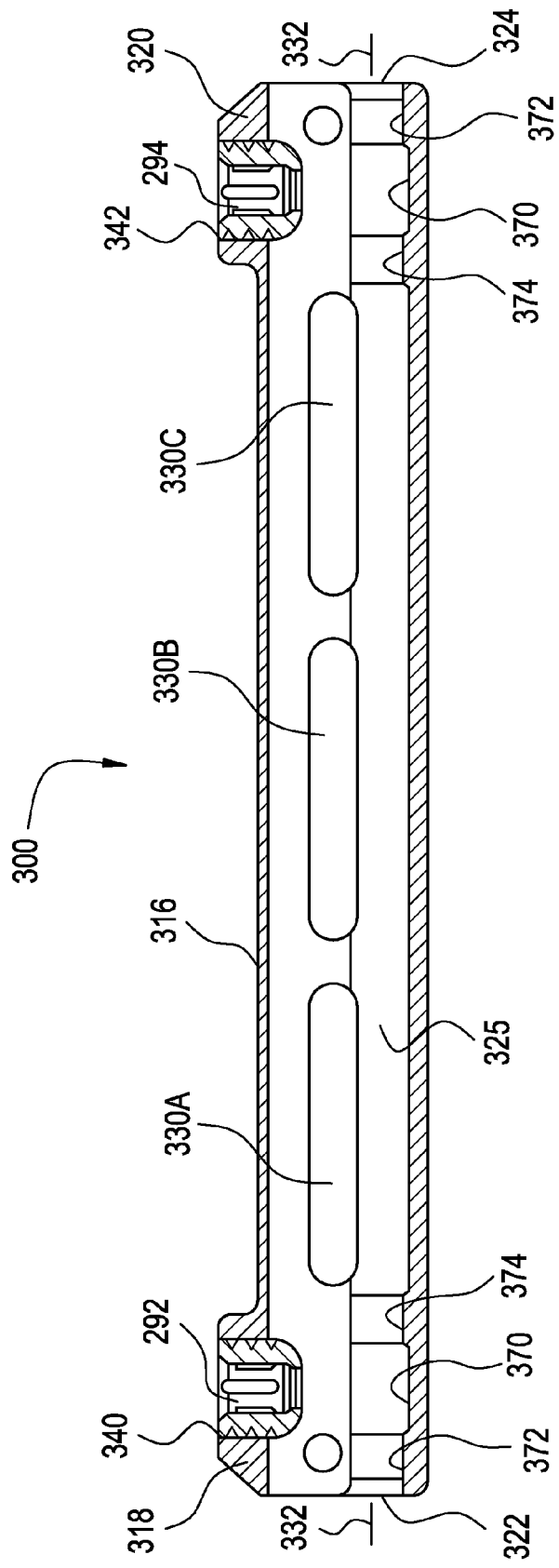
FIG. 14C is a side view in cross section of the connector of FIG. 14A taken along the lines F-F of FIG. 14B.
Figure 14D:
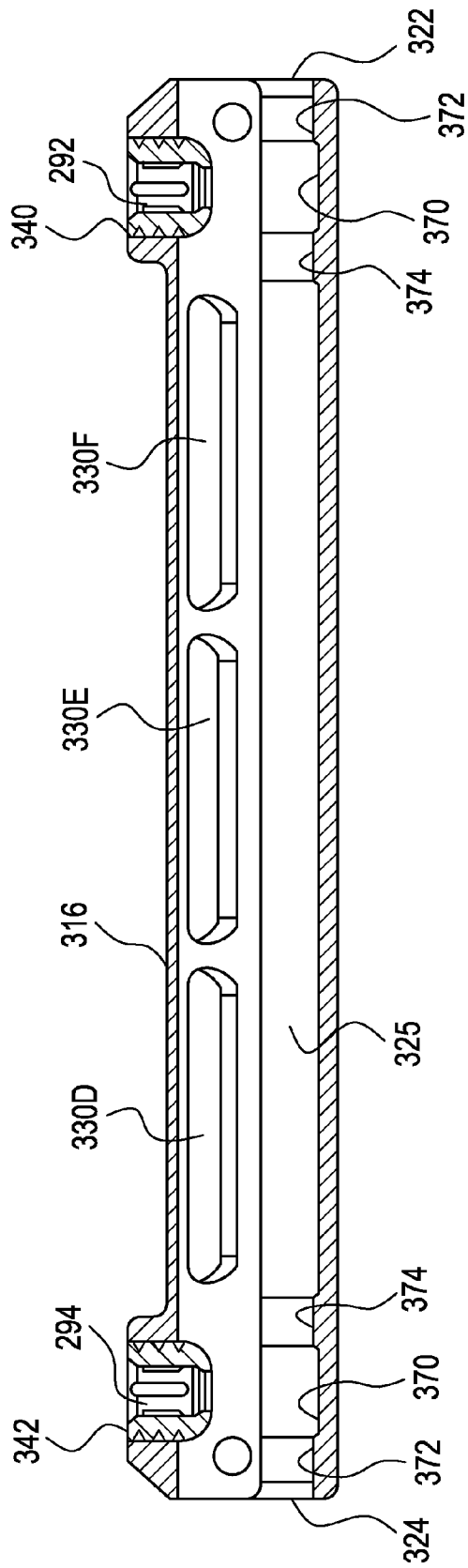
FIG. 14D is a side view in cross section of the connector of FIG. 14A taken along the lines G-G of FIG. 14B.
Figure 14E:
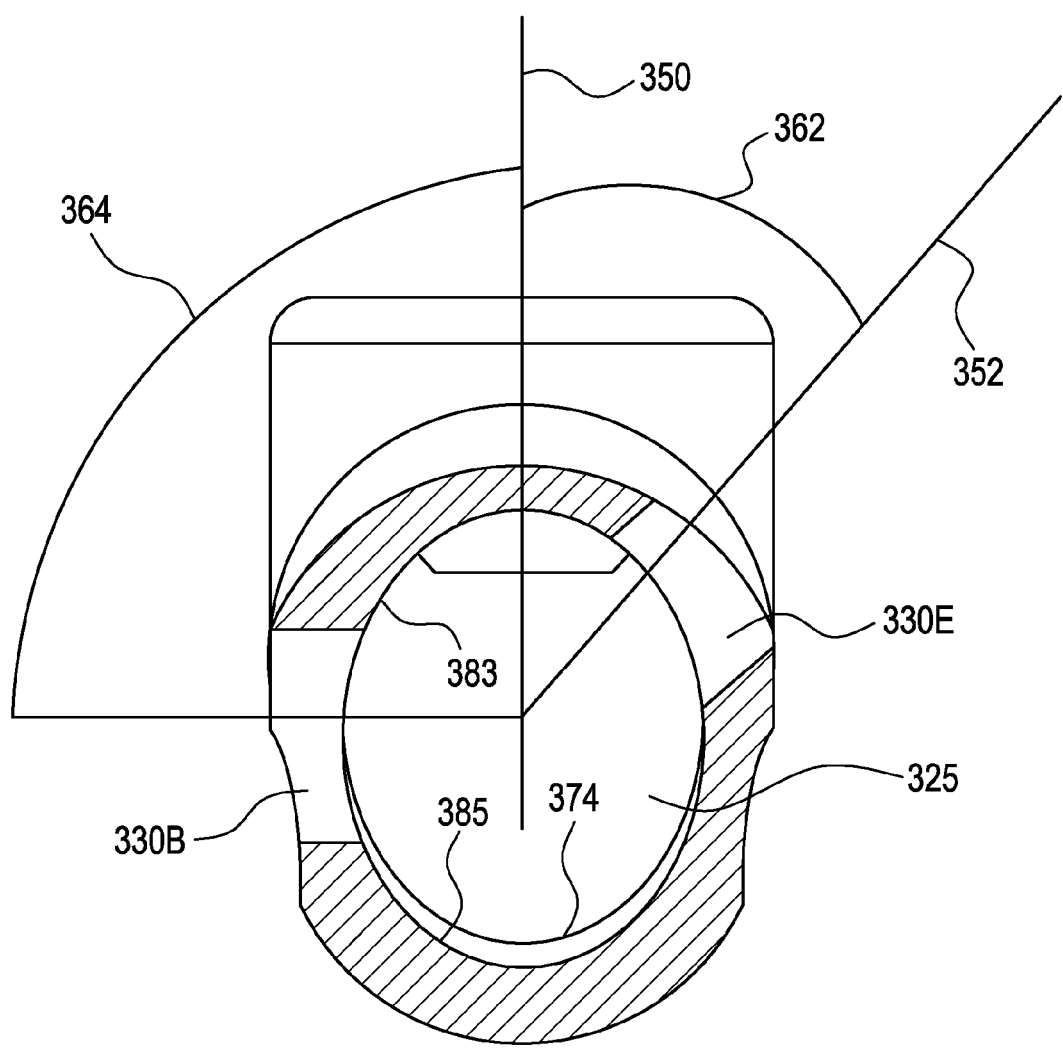
FIG. 14E is an end view in cross section of the connector of FIG. 14A taken along the lines H-H of FIG. 14A.
Figure 14F:
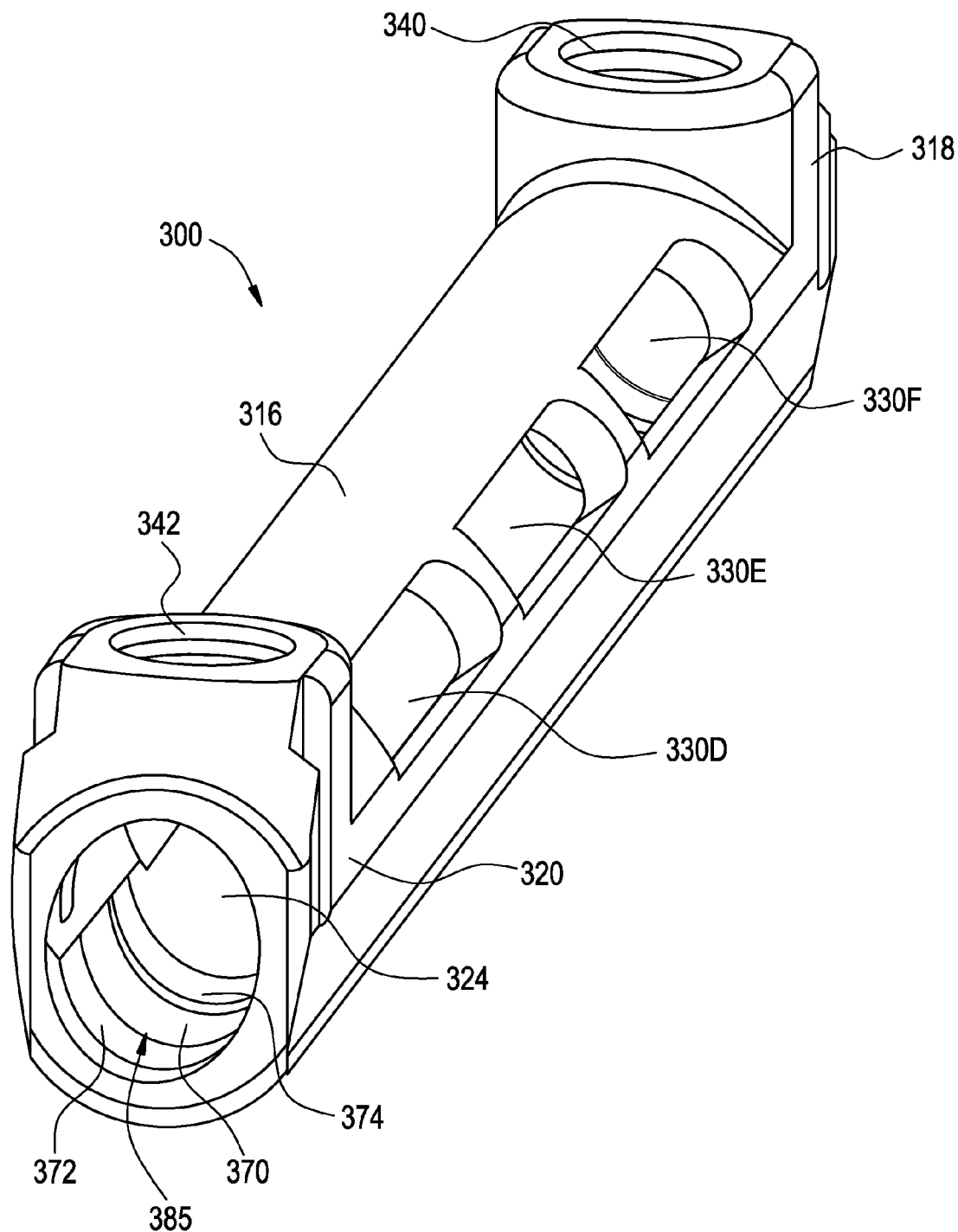
FIG. 14F is a perspective view of the connector of FIG. 14A.

FIGS. 14A-14F illustrate another exemplary embodiment of a rod-to-rod connector 300 for connecting a first spinal rod to a second rod in an end-to-end, e.g., tandem, arrangement for permitting subsequent adjustment of one or both of the spinal rods relative to each other and to the connector. The illustrated exemplary connector 300 may be similar in construction and use to the exemplary connector 10 discussed in detail above. For example, the exemplary connector 300 may comprise a body 316 having a first end 318 and a second end 320 spaced apart from the first end 318 of the connector 310. The first end 318 of the body 316 of the exemplary connector 300 may have a first rod opening 322 formed therein for receiving the first spinal rod and the second end 320 of the body 316 may have a second rod opening 324 formed therein for receiving the second rod. The body 316 of the connector 300 may have a passage 325 extending between the first rod opening 322 and the second rod opening 324 in which a portion of the first rod and a portion of the second rod may be positioned. The body 316 of the connector 300 may have a first closure mechanism receiving opening 340 and a second closure mechanism receiving opening 342. The first closure mechanism receiving opening 340 may communicate with the passage 325 receiving the first spinal rod to allow delivery of a closure mechanism, for example set screw 292, for locking the position of the first spinal rod within the passage 325. The second closure mechanism receiving opening 342 may communicate with the passage 325 receiving the second spinal rod to allow delivery of a closure mechanism, for example set screw 294 for locking the position of the second spinal rod within the passage 325. The first closure mechanism receiving opening 340 and the second closure mechanism receiving opening 342 may be oriented to facilitate placement of the closure mechanisms from the top of the connector. For example, the first closure mechanism receiving opening 340 and the second closure mechanism receiving opening 342 may be oriented in a first plane 350 that intersects the longitudinal axis 332 of the passage and the top surface of the body 316 of the connector 300, as illustrated in FIG. 14E.

The illustrated exemplary connector 300 includes two sets of adjustment openings—a first set of spaced-apart adjustment openings 330A-C and a second set of spaced-apart adjustment openings 330D-F. The adjustment openings 330A-F are oriented along the length of the body 316 of the connector 300 between the first end 318 and the second end 320 of the body 316 of the connector 300. The adjustment openings 330A-F communicate with the passage 325 within the body 316 in which a portion of the first rod and the second rod may be positioned to allow a portion of an adjustment instrument or other instruments to access the passage 325 and one or more rods within the passage 325.

The second set of adjustment openings 330D-F may be oriented to facilitate access to the passage 325 and the spinal rods therein from the top of the connector. Preferably, the first closure mechanism receiving opening 340 and the second closure mechanism receiving opening 342 and the second set of adjustment openings 330D-F are oriented to facilitate access to the respective openings from the top of the connector preferably without necessitating rotation or other adjustment of the connector 300. The second set of adjustment openings 330D-F may be oriented in a second plane 352 that intersects the first plane 350 and the adjustment opening 330. In the illustrated exemplary embodiment, the second plane 352 may intersect the first plane 350 proximate the longitudinal axis 332 of the passage 325. The second plane 352 may be oriented at a first angle 362 to the first plane 350. The first angle 362 may be greater than approximately 0 degrees. In certain exemplary embodiments, the first angle 362 may be greater that approximately 0 degrees and less than or equal to approximately 90 degrees and preferably may be between approximately 20 degrees and approximately 70 degrees.

In certain procedures, it may desirable to reduce the profile of a rod-to-rod connector within the body by rotating the connector about the axis of the connector to a reduced profile orientation. In the case of the exemplary connector 300, for example, rotation of the connector 300 approximately ninety degrees (90°) from the orientation illustrated in FIG. 14E orients the connector 300 in a reduced profile orientation. The first set of adjustment openings 330A-C may be oriented in a third plane 354 that intersects the first plane 350 and the adjustment openings 330 A-C to facilitate access to the respective openings from the top of the connector 300 when the connector is in a reduced profile orientation. In the illustrated exemplary embodiment, the third plane 354 may intersect the first plane 350 proximate the longitudinal axis 332 of the passage 325. The third plane 354 may be oriented at a second angle 364 to the first plane 350 that is selected to permit access to the openings when the connector is oriented in a reduced profile orientation. In the exemplary embodiment, for example, the second angle 364 is approximately 90 degrees. Rotation of a connector to a reduced profile orientation may necessitate the use of an angled driver instrument to insert or remove the first and second set screws 290 and 292.

The passage of a rod-to-rod connector disclosed herein (e.g., connector 10, connector 200, or connector 300) may be configured to facilitate seating and fixing a spinal rod to the connector. In the exemplary embodiment, for example, the passage 325 of the connector 300 proximate the first rod opening 322 and the second rod opening 324 may include a recess 370 to create spaced-apart, along the longitudinal axis of the passage 325, spinal rod contact surfaces 372 and 374. The recess 370 is preferably positioned within the passage 325 approximately opposite the closure mechanism, e.g., the set screw 292 and/or 294, such that tightening of the closure mechanism against the spinal rod causes the rod to deform by bending into the recess 370. In this manner, increased resistance to motion, e.g., axial slip, of the spinal rod relative to the connector may be achieved.

To further facilitate seating and fixing of the spinal rod relative to a connector (e.g., connector 10, connector 200, or connector 300), one or both of the rod openings of the connector may be configured to create an interference fit between the rod and the connector upon tightening of the closure mechanism against the rod. In the exemplary connector 300, for example, the first rod opening 322 and/or the second rod opening 324 and/or a portion of the length of the passage 325 may be formed from two non-concentric arcuate sections: a upper arcuate section 383 and a lower arcuate section 385. The radius of the upper arcuate section 383 may be greater than the radius of the spinal rod to facilitate placement of the spinal rod within the connector. The radius of the lower arcuate section 385 may be less than or equal to the radius of the spinal rod and less than or equal to the radius of the upper arcuate section 383. For a 4.5 mm diameter rod, for example, the radius of the lower arcuate section 385 may be approximately 0.05 mm less than the radius of the spinal rod. Tightening of the closure mechanism against the spinal rod cause the spinal rod to engage the lower arcuate section in an interference fit inhibiting motion of the spinal rod relative to the connector. The resultant force on the spinal rod, and the closure mechanism when tightened against the spinal rod, caused by interference fit may reduce back-out of closure mechanism.

Figure 15A:
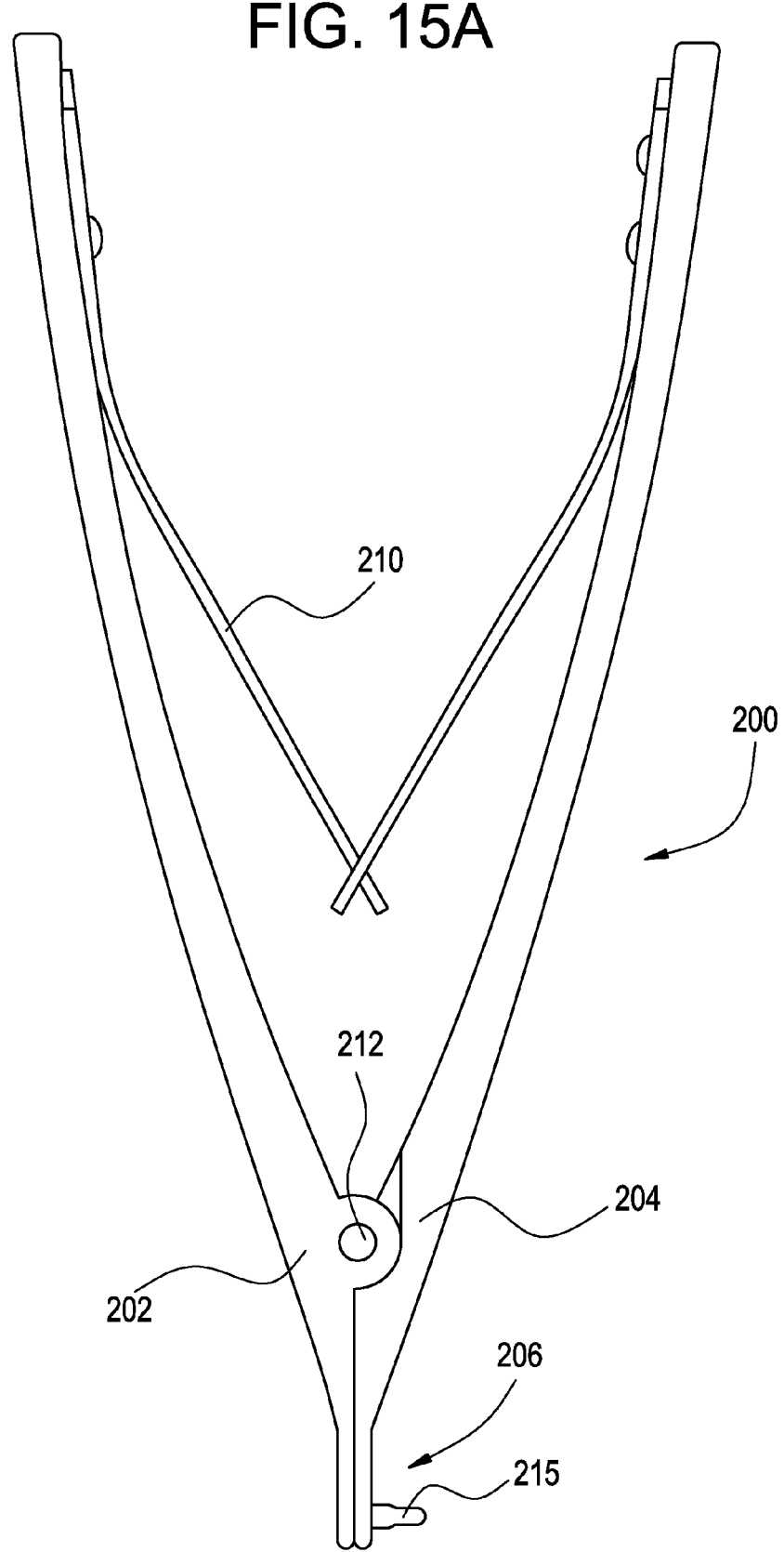
FIG. 15A is a right side view of another exemplary embodiment of an adjustment instrument.
Figure 15B:
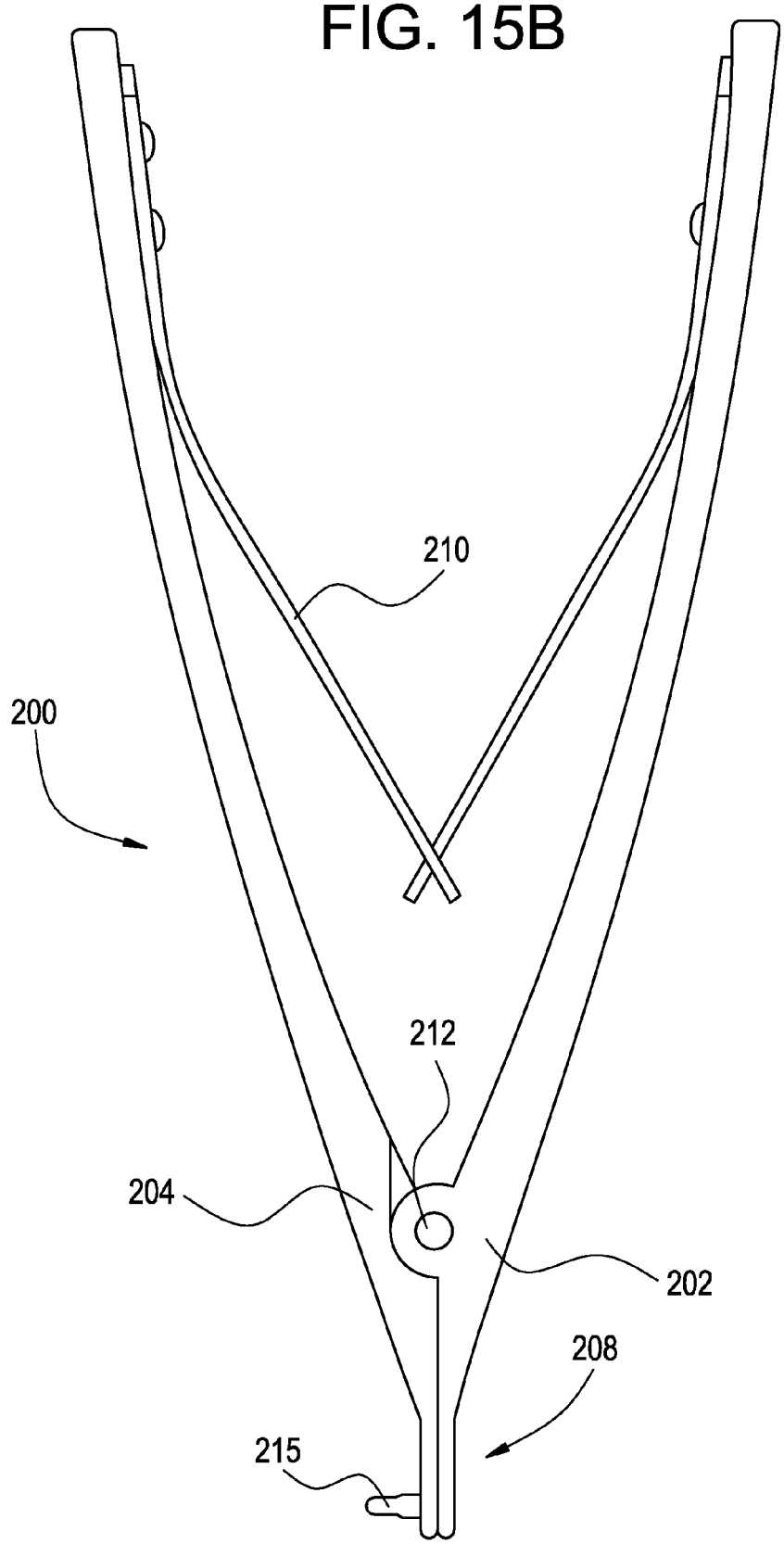
FIG. 15B is a left side view of the adjustment instrument of FIG. 15.

FIGS. 15A-B illustrates another exemplary embodiment of an adjustment instrument 200 having a first arm 202 pivotally connected to a second arm 204. The distal end 206 of the second arm 204 of the adjustment instrument 200 may include a first foot 215 oriented approximately perpendicular to the distal end 206 of the second arm 204. As in the exemplary embodiment illustrated in FIG. 12, the first foot 215 may be oriented generally parallel to the longitudinal axis of the passage of a connector, such as the exemplary connector 10, when the first foot 215 is positioned in the passage. The length of the first foot 215 may be selected to be greater than or equal to the space between adjacent openings 30 of the connector. In contrast to the exemplary embodiment illustrated in FIG. 12, the distal end 208 of the first arm 202 may lack a foot and, thus, the instrument 200 may have only a single foot, first foot 215. In use, manipulation of the proximal ends of the first arm 202 and second arm 204 together causes the distal ends 206, 208 to pivot about pivot pin 212 and separate from one another to provide for distraction of one or more rods positioned within the passage of a connector. The instrument 200 may include a spring 210 or the like to bias the distal ends 206, 208 towards one another.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A connector for connecting a first spinal rod to a second spinal rod, the connector comprising:
   a body having a first end and a second end spaced apart from the first end, the first end of the body having a first rod opening formed therein for receiving the first spinal rod, the second end having a second rod opening formed therein for receiving the second rod, the body having a passage extending between the first opening and the second opening,
   the body having a first plurality of spaced apart adjustment openings oriented on a common axis along the length of the body between the first end and the second end, the first plurality of adjustment openings communicating with the passage,
   the body having a second plurality of spaced apart adjustment openings oriented on a common axis along the length of the body between the first end and the second end, the second plurality of adjustment openings communicating with the passage,
   the body having a first closure mechanism receiving opening positioned proximate the first end and intersecting the passage and a second closure mechanism receiving opening positioned proximate the second end and intersecting the passage, the first closure mechanism receiving opening and the second closure mechanism receiving opening each including an internal thread,
   the first closure mechanism receiving opening and second closure mechanism receiving opening oriented in a first plane, the first plurality of adjustment openings oriented in a second plane, the second plurality of adjustment openings oriented in a third plane, the second plane and the third plane oriented at an angle greater than 0 degrees to each other and to the first plane,
   a first set screw having an external thread engageable with the internal thread of the first closure mechanism receiving opening, at least a portion of the first set screw being deliverable through the first closure mechanism receiving opening into the passage, and
   a second set screw having an external thread engageable with the internal thread of the second closure mechanism receiving opening, at least a portion of the second set screw being deliverable through the second closure mechanism receiving opening into the passage.

2. The connector of claim 1, wherein the angle between the first plane and the third plane is between approximately 20 degrees and approximately 70 degrees.

3. The connector of claim 2, wherein the angle between the second plane and the third plane is greater than 45 degrees.

4. The connector of claim 2, wherein the angle between the first plane and the third plane is approximately 90 degrees.

5. The connector of claim 1, wherein the first rod opening is circular, elliptical, polygonal, or square in shape.

6. The connector of claim 5, wherein the second rod opening has an approximately corresponding size and shape to the first rod opening.

7. The connector of claim 5, wherein the second rod opening has at least one of a distinct size and distinct shape compared to the first rod opening.

8. The connector of claim 1, wherein at least one of the first end and the second end is sloped.

9. A connector for connecting a first spinal rod to a second spinal rod, the connector comprising:
   a body having a first end and a second end spaced apart from the first end, the first end of the body having a first rod opening formed therein for receiving the first spinal rod, the second end having a second rod opening formed therein for receiving the second rod, the body having a passage extending between the first opening and the second opening,
   the body having an adjustment opening oriented along the length of the body between the first end and the second end, the adjustment opening communicating with the passage,
   the body having a first closure mechanism receiving opening positioned proximate the first end and intersecting the passage and a second closure mechanism receiving opening positioned proximate the second end and intersecting the passage, the first closure mechanism receiving opening and second closure mechanism receiving opening being oriented in a first plane and the adjustment opening being oriented in a second plane, the second plane being oriented at an angle greater than zero to the first plane, the first closure mechanism receiving opening and the second closure mechanism receiving opening each including an internal thread, the body lacking an adjustment opening oriented in a plane parallel to the first plane,
   a first set screw having an external thread engageable with the internal thread of the first closure mechanism receiving opening, at least a portion of the first set screw being deliverable through the first closure mechanism receiving opening into the passage, and
   a second set screw having an external thread engageable with the internal thread of the second closure mechanism receiving opening, at least a portion of the second set screw being deliverable through the second closure mechanism receiving opening into the passage.

10. The connector of claim 9, wherein the angle between the first plane and the second plane is less than 90 degrees.

11. The connector of claim 9, wherein the angle between the first plane and the second plane is between approximately 20 degrees and approximately 70 degrees.

12. A spinal system for connecting a first vertebra to a second vertebra, the system comprising:
   a first bone anchor for coupling to a first vertebra;
   a second bone anchor for coupling to a second vertebra;
   a first spinal rod for coupling to the first bone anchor;
   a second spinal rod for coupling to the second bone anchor;
   a connector for connecting the first spinal rod to the second spinal rod, the connector comprising:
      a body having a first end and a second end spaced apart from the first end, the first end of the body having a first rod opening formed therein for receiving the first spinal rod, the second end having a second rod opening formed therein for receiving the second rod, the body having a passage extending between the first opening and the second opening,
      the body having a first plurality of spaced apart adjustment openings oriented on a common axis along the length of the body between the first end and the second end, the first plurality of adjustment openings communicating with the passage,
      the body having a second plurality of spaced apart adjustment openings oriented on a common axis along the length of the body between the first end and the second end, the second plurality of adjustment openings communicating with the passage,
      the body having a first closure mechanism receiving opening positioned proximate the first end and intersecting the passage and a second closure mechanism receiving opening positioned proximate the second end and intersecting the passage,
      the first closure mechanism receiving opening and second closure mechanism receiving opening oriented in a first plane, the first plurality of adjustment openings oriented in a second plane, the second plurality of adjustment openings oriented in a third plane, the second plane and the third plane oriented at an angle greater than 0 degrees to each other and to the first plane,
      a first closure mechanism deliverable through the first closure mechanism receiving opening into contact with the first rod when the first rod is positioned within the passage, and
      a second closure mechanism deliverable through the second closure mechanism receiving opening into contact with the second rod when the second rod is positioned within the passage.

13. The spinal system of claim 12, wherein the first spinal rod has a first size and the second spinal rod has a second size distinct from the first size.

14. A spinal system for connecting a first vertebra to a second vertebra, the spinal system comprising:
   a first bone anchor for coupling to a first vertebra;
   a second bone anchor for coupling to a second vertebra;
   a first spinal rod for coupling to the first bone anchor;
   a second spinal rod for coupling to the second bone anchor;
   a connector for connecting the first spinal rod to the second spinal rod, the connector comprising:
      a body having a first end and a second end spaced apart from the first end, the first end of the body having a first rod opening formed therein for receiving the first spinal rod, the second end having a second rod opening formed therein for receiving the second rod, the body having a passage extending between the first opening and the second opening,
      the body having an adjustment opening oriented along the length of the body between the first end and the second end, the adjustment opening communicating with the passage,
      the body having a first closure mechanism receiving opening positioned proximate the first end and intersecting the passage and a second closure mechanism receiving opening positioned proximate the second end and intersecting the passage, the first closure mechanism receiving opening and second closure mechanism receiving opening being oriented in a first plane and the adjustment opening being oriented in a second plane, the second plane being oriented at an angle greater than zero to the first plane, the body lacking an adjustment opening oriented in a plane parallel to the first plane,
      a first closure mechanism deliverable through the first closure mechanism receiving opening into contact with the first rod when the first rod is positioned within the passage, and
      a second closure mechanism deliverable through the second closure mechanism receiving opening into contact with the second rod when the second rod is positioned within the passage.

\* \* \* \* \*